(12) United States Patent
Bullock et al.

(10) Patent No.: US 7,259,016 B2
(45) Date of Patent: Aug. 21, 2007

(54) SHAKEN NOT STIRRED

(75) Inventors: William Paul Bullock, Ames, IA (US); Kathy Jo Cook, Slater, IA (US); Julie Lynne Ritland, Hubbard, IA (US); John Michael Gass, Slater, IA (US)

(73) Assignee: Syngenta (AT) Limited, Surrey (GB)

( * ) Notice: Subject to any disclaimer, the term of this patent is extended or adjusted under 35 U.S.C. 154(b) by 204 days.

(21) Appl. No.: 09/886,937

(22) Filed: Jun. 21, 2001

(65) Prior Publication Data

US 2003/0180951 A1 Sep. 25, 2003

Related U.S. Application Data

(60) Provisional application No. 60/213,036, filed on Jun. 21, 2000.

(51) Int. Cl.
*A01H 1/00* (2006.01)
*C12N 15/82* (2006.01)
*C12N 15/87* (2006.01)

(52) U.S. Cl. .................. 435/470; 435/468; 435/430; 800/278; 800/312; 800/300.1; 800/306; 800/293

(58) Field of Classification Search ............... 435/468, 435/430, 470, 419; 800/277, 312, 306, 300.1
See application file for complete search history.

(56) References Cited

U.S. PATENT DOCUMENTS

| 4,743,548 A | 5/1988 | Crossway et al. |
| 5,302,523 A | 4/1994 | Coffee et al. |
| 5,464,765 A | 11/1995 | Coffee et al. |

FOREIGN PATENT DOCUMENTS

| EP | 0 485 506 B1 | 12/1997 |
| WO | WO94/28148 | * 8/1994 |
| WO | PCTUS 99/01815 | 8/1999 |

OTHER PUBLICATIONS

Hansen et al., 1999, Trends in plant Science, vol. 4, pp. 226-231, see p. 230.*
(see Cole-Parmer Instrument Company catalogue information on "shakers", attached; see also coleparmer.com/catalogue/0304, Feb. 1, 2005).*
Bullock, W.P., D. Foster, T. Friend, A. Greenland, D. Dias, and V. Kaster. Transgene Silencing in Maize: Phenotypic Segregation Analysis. Illinois Plant Breeder School Proceedings: 157-190 (1998).
Register, J.C., D.J. Petterson, P.J. Bell, W.P. Bullock, I.J. Evans, B. Frame, A.J. Greenland, N.S. Higgs, I. Jepson, S. Jiao, C.J. Lewnau, J.M. Sillick. and H.M. Wilson. Structure and Function of Selectable and Non-Selectable Transgenes in Maize After Introduction by Particle Bombardment. Plant Molecular Biology 23: 951-961 (1994).
Chu Chih-Chingt. The $N_6$ Medium and Its Applications to Anther Culture of Cereal Crops. Institute of Botany, Academia Sinica, 43-50.
Murashige, T. and F. Skoog. A Revised Medium for Rapid Growth and Bioassays with Tobacco Tissue Cultures. Physiol. Plant 15: 473-497 (1962).
Gerald L. Vaughan, Jacqueline Jordan, and Susan Karr. The Toxicity, in Vitro, of Silicon Carbide Whiskers. Environmental Research 57-60 (Dec. 4, 1990).
Armstrong, C.L. The First Decade of Maize Transformation: A Review and Future Perspective. Maydica 44: 101-109 (1999).
Asano, Y., Y. Otsuki, and M. Ugaki. Electroporation-Mediated and Silicon Carbide Fiber-Mediated DNA Delivery in *Agrostis alba* L. (Redtop). Plant Science 79: 247-252 (1991).
Brisibe, E.A., A. Gajdosava, A. Olesen, and S.B. Andersen, Cytodifferentiation and Transformation of Embryogenic Callus Lines Derived from Anther Culture of Wheat. Journal of Experimental Botany 51: 187-196 (2000).
Dalton, S.J., A.J .E. Bettany, E. Timms, and P. Morris. Transgenic Plants of Lolium multiflorum, Lolium perenne, Festuca arundinacea, and Agrostis stolonifera by Silicon Carbide Fibre-Mediated Transformation of Cell Suspensions. Plant Science 132: 31-43 (1997).
Dunahay, T.G. Transformation of *Chlamydomonas reinhardtii* with Silicon Carbide Whiskers. Biotechniques 15: 452-460 (1993).
Dunahay, T.G., S.A. Adler, J.W. Jarvik. Transformation of Microalage Using Silicon Carbide Whiskers. Methods in Molecular Biology, vol. 62: Recombinant Gene Expression Protocols, pp. 503-509 (1997).
Finer, J.J. and M.D. McMullen. Transformation of Soybea-n Via Particle Bombardment of Embryogenic Suspension Culture Tissue. In Vitro Cell. Dev. Biol. 27P:175-182 (1991).
Finer, J.J., K.R. Finer, and E.R. Santarem. Plant Cell Transformation, Physical Methods for. Encyclopedia of Molecular Biology and Molecular Medicine vol. 4: Mass Spectrometry High Speed DNA Fragment Sizing to Plasma Lipoproteins, pp. 458-465 (1996).
Frame, B. R., P. Drayton, S. Bagnall, C. Lewnau, P. Bullock, M. Wilson, J. Dunwell, J. Thompson, and K. Wang. Production of Fertile Transgenic Maize Plants by Silicon Carbide Whisker Mediated Transformation. The Plant Journal 6: 941-948 (1994).
Kaeppler, H.F., W. Gu, D.A. Somer, H.W. Rines, and A. Cockburn. Silicon Carbide Fiber-Mediated DNA Delivery into Plant Cells. Plant Cell Reports 9: 415-418 (1990).
Kaeppler, H.F., D.A. Somers, H. W. Rines, and A. Cockburn. Silicon Carbide Fiber-Mediated Stable Transformation of Plant Cells. Theoretical and Applied Genetics. 84: 560-566 (1992).
Matsushita, J., M. Otani, Y. Wakita, O. Tanaka, and T. Shimada. Transgenic Plant Regeneration Through Silicon Carbide Whisker-Mediated Transformation of Rice (Oryza Sativa L.). Breeding Science 49: 21-26 (1999).
Nagatani, N., H. Honda, T. Shimada, and T. Kobayashi. DNA Delivery Into Rice Cells and Transformation Using Silicon Carbide Whiskers. Biotechnology Techniques. 11:471-473 (1997).

(Continued)

*Primary Examiner*—David T. Fox
*Assistant Examiner*—Georgia Helmer
(74) *Attorney, Agent, or Firm*—Dana S Rewoldt

(57) ABSTRACT

This invention relates to a method of transforming plant cells using whiskers on various types of target tissue. And further relates to a method of transforming plant cells using whiskers with an improved agitation method.

5 Claims, 2 Drawing Sheets

OTHER PUBLICATIONS

Parrott, W.A., J.N. All, M.J. Adang, M.A. Bailey, H.R. Boerma, and C.N. Stewart, Jr. Recovery and Evaluation of Soybean Plants Transgenic for a Bacillus thuringiensis_var. Kurstaki Insecticidal Gene. Society for In Vitro Biology 144-149 (May 14, 1993).

Petolino, J.F., N.L. Hopkins, B.D. Kosegi, M. Skokut. Whisker Mediated Transformation of Embryogenic Callus of Maize. Plant Cell Reports 19 (8): 781-786 (2000).

Roeckel, P., P. Heizmann, M. Dubois, and C. Dumas. Attempts to Transform Zea mays via Pollen Grains. Sex. Plant Reprod. 1:156-163 (1988).

Serik, O., I. Ainur, K. Murat, M. Tetsuo, and I. Masaki. Silicon Carbide Fiber-Mediated DNA Delivery into Cells of Wheat (*Triticum aestivum* L.) Mature Embryos. Plant Cell Reports 16: 133-136 (1996).

Soloki, M., P.G. Alderson, and G Tucker. Genetic Transformation of Grape Using Agrobacterium and Silicon Carbide Whiskers. In M.R. Davey, P.G. Anderson, K.C. Lowe (Eds) Tree Biotechnology: Towards the Millennium. pp. 325-330. (1998). *Vortex Mixer* (*Genie II*).

Songstad, D.D., D.A. Somers, and R.J. Griesbach. Advances in Alternative DNA Delivery Techniques. Plant Cell, Tissue and Organ Culture 40: 1-15 (1995).

Southgate, E.M., M.R. Davey, J.B. Power, and R.J. Westcott. A Comparison of Methods for Direct Gene Transfer into Maize (*Zea mays* L.). In Vitro Cell. Dev. Biol.- Plant 34:218-224 (1998).

Spangenberg, G. Application of Biotechnology in Pasture Plant Improvement. Proc. of Int'l Workshop Utilization of Transgenic Plant and Genome Analysis in Forage Crops, p. 9-30, Nishinasuno, Tochigi, Japan (1998).

Takahashi, W., T. Shimada, J. Matsushita, and O. Tanaka. Aluminium Borate Whisker-Mediated DNA Delivery into Callus of Rice and Production of Transgenic Rice Plant. Plant Prod. Sci. 3: 219-224 (2000).

Thompson, J.A., P.R. Drayton, B.R. Frame, K. Wang, and I.M. Dunwell. Maize Transformation Utilizing Silicon Carbide Whiskers: A Review. Euphytica 85: 75-80 (1995).

Wang, K., P. Drayton, B. Frame, J. Dunwell, and J.A. Thompson. Whisker-Mediated Plant Transformation: An Alternative Technology. In Vitro Cellular and Developmental Biology 31: 101-104 (1995).

Armstrong, Charles L. Transgenic Corn: Ten Years Down, What Will the Next Ten Bring? 54th Annual Corn & Sorghum Research Conference. 124-135.

Green, C.E. and Rhodes, C.A. Plant Regeneration in Tissue Cultures of Maize. Department of Agronomy and Plant Genetics, University of Minnesota. 367-372 (1982).

Rédel, George P. Genetics Manual, Current Theory, Concepts, Terms. University of Missouri, World Scientific Publishing Co. Pte. Ltd. (1998).

Warren, G. S., Thomas, Pious, Herrera, M. Hill, S.J. and Terry, R. F. the Use of Plant Cell Cultures for Studying Virus Resistance, and Enhancing the Production of Virus-Resistant and Virus-Free Plants. Journal of Biotechnology 171-201 (1992).

Appel, J.D., T.M. Fasy, D.S. Kohtz, E.M. Johnson. Asbestos Fibres Media Transformation of Monkey Cells by Exogenous Plasmid DNA. Proc. Natl. Acad. Sci. 85:7670-7674 (1988).

Costanzo, Maria C. and Fox, Thomas D. Transformation of Yeast by Agitation With Glass Beads. Genetics 120: 667-670 (Nov. 1988).

Fechheimer, M., Boylan, J.F. Parker, S. Sisken, J.E., Patel, G.L. and Zimmer, S.G. Transfection of Mammalian Cells with Plasmid DNA by Scrape Loading and Sonication Loading. Proc. Natl. Acad. Sci. USA, vol. 84, pp. 8463-8467 (Dec. 1987).

Fang-Sheng Wu and Harry H. Murakishi. Infection and Synthesis Rate of Southern Bean Mosaic Virus in Soybean Callus Cells under Selected Cultural Conditions. Journal Series Article 8190 of the Michigan Agricultural Experiment Station. 1389-1392 (Mar. 14, 1978).

Jessica Morrison Silva. Diligence and Ingenuity Pay Off in a Genetic Engineering Laboratory. Americans in Agriculture Portraits of Diversity 114-116 (1990).

P.J. Harest, D. Lachance, C. Jones and Y. Davantier. Microprojectile and Silicong Carbide Mediated DNA delivery in Conifers and recovery of Transgenic Black Spruce (*Picea mariana*). Poster for Gordon Conference, Ontario, Canada, 1 page.

R. C. Brown, J. A. Hoskins and J. Young. Not Allowing the Dust to Settle. Chemistry in Britain, 6 pages (Oct. 1992).

B. Alberts, D. Bray, J. Lewis, M. Raff, K. Roberts and J. D. Watson. Special Features of Plant Cells. Molecular Bilogy of The Cell, Garland Publishing, Inc. (2$^{nd}$ Edition) p. 1099 (1983).

Ingo Potrykus. *Gene Transfer to Cereals: An Assessment.* Biotechnology, Vo. 8., 535-542 (Jun. 1990).

Gunther Neuhaus, Gabriele Neuhaus-Url, Egon J. De Groot and Hans-Georg Schweiger. High Yield and Stable Transformation of the Unicellular Green Alga Acetabularia by Microinjection of SV40 DNA and pSV2neo. IRL Press Limited, Oxford, England. The EMBO Journal, vol. 5, No. 7, 1437-1444 (1986).

Arthur and Elizabeth Rose. *The Condensed Chemical Dictionary*, Reinhold Publishing Corporation, New York, Seventh Edition (1966).

Colin Ilett. *Silicon Carbide Fibre Mediated DNA Transformation of Zea mays.* 1-39 (Jun. 1992).

Chu, C.C., C.C. Wang, C.S. Sun, C. Hsu, K.C. Yin, C. Y. Chu, F. Y. Bi. Establishment of an Efficient Medium for Anther Culture of Rice Through Comparative Experiments on Nitrogen Sources. Sci. Sinica. 18: 659-668 (1975).

\* cited by examiner

SHAKEN NOT STIRRED

PRIORITY CLAIMS

This application is claiming priority from the provisional U.S. application filed Jun. 21, 2000 application 60/213,036.

FIELD OF THE INVENTION

This invention relates to a method of transforming plant cells using whiskers on various types of target tissue. And further relates to a method of transforming plant cells using whiskers with an improved agitation method.

BACKGROUND OF THE INVENTION

Since the early 1980's scientists have been seeking new and better methods for transforming plants of all type. Initially, dicots were more readily transformed and monocots were fairly difficult. However, in the last ten years methods of transforming both types of plants have been achieved. In light of these achievements the choice of method for the transformation of plant cells tends to be limited to those which are convenient for the target plant type. As a generalisation, research in transformation has focused on new techniques which improve the usefulness of the transformation methods. Several transformation methods which have been available for introduction of foreign DNA include: *Agrobacterium* technology (U.S. Pat. No. to 5,591,616 to Japan Tobacco); electroporation technology (U.S. Pat. No. 5,679,588 to PGS), and microinjection. This last method known as "microinjection" is where a DNA construct is injected from a hollow needle into a target cell. A variant of that procedure is the rupturing of the cell wall with a needle, the DNA being added to the surrounding medium and allowed to diffuse into the cell through the break in the cell wall. This is known as "micropricking". Both of these procedures require a high degree of manipulative skill by the operator and are very time consuming.

The most well known transformation approach may be the biolistic bombardment. In this method microparticles coated with DNA are accelerated and blasted into cells (U.S. Pat. No. 4,945,050 to Cornell and U.S. Pat. No. 5,538,877 to Dekalb). This approach abandons the high precision of targeting which is inherent in microinjection and micropricking, in favour of a rapid "shotgun" approach which blasts large numbers of cells in a short time, giving a larger number of putative transformants for screening.

In such an approach, tungsten or gold microspheres, coated with DNA are fired at target tissue at very high velocity, for example under propulsion of an explosive charge. One problem with this technique is the effect of the blast on the target tissue.

The most closely related technology to the present invention is another transformation method that involves the use "whiskers" to transform (U.S. Pat. Nos. 5,302,523 and 5,463,765 to Zeneca and PCT/US99/01815 to Dow Agrosciences LLC). In this approach there was provided a method of transforming cells comprising contacting the cells with a multiplicity of needle-like bodies so that the cells are impaled upon the bodies, transforming DNA being either surface-bound to the projections or present in a liquid medium in contact therewith.

In one embodiment a quantity of the needle-like bodies was added to a liquid suspension of the cells to be transformed and the mixture agitated, for example by stirring, so that the moving cells and bodies interact resulting in penetration of the cell wall of the cells.

However, this whisker method lacked efficiency. Even when the first applications were filed it was realized that efficiency could come from all different aspects of whiskering.

At that time the Zeneca application stated was stated that, It has been found that the efficiency of DNA delivery varies according to the conditions; it is affected by several factors including the following: vortex time; cell suspension type (variation also found by H. F. Kaeppler et al, 1990, Plant Cell Reports, 9, 415-418); cell suspension age; osmolarity of culture medium; type of fibres; number of fibres present; type of DNA construct; concentration of DNA. Other factors which may affect DNA delivery include: the physical mixing methods used; the size, shape and uniformity of the fibres; the topology of the DNA (eg. linear, supercoiled); the presence of "carrier" DNA alongside the transforming DNA.

What was not discovered or suggested was that a change in the agatition step would substantially reduce, by a third at least, the time and effort needed to complete whisker mediated transformation of cells.

Another method used through out PCT/US 99/01815 to Dow Agrosciences LLC comprised mixing the DNA and fibre suspension, then adding this mixture to the target tissue. The final mixture was vortexed together. The cells were then incubated, and tested for expression of recombinant DNA and regenerated into transgenic plants.

Throughout the application underlying PCT/US 99/01815 the examples are attempting to optimize the production of small quantities of transformants using the Whisker transformation process through, for example, use of osmotic treatments, testing vessels and varying agitation (vortexing) time (see Table 9 in PCT/US 99/01815). In table nine the effect of vortexing time on the transformation of rice showed that 15 seconds of vortexing resulted in twice as much Gus expression as did 120 seconds of vortexing. The expression of the transformed gene in the small microfuge tubes decreased with each increase in vortexing time. Thus increased agitation by vortexing led to less positive transformation results. Therefore altering the type of agitation from vortexing to a more robust, or violent agitation method seemed an unlikely way of increasing production of transformants.

Thus there remained a need for a new technique within a whisker method that permits large amounts of target tissue to be transformed more effectively.

Additionally, there remains a need for an improvement in the whisker method that allows previously incompetent tissue (or tissue with very low transformant yield) to be more effectively transformed with whiskers.

Furthermore, there remained a need for a method that more effectively accesses whiskers and DNA to most of the surface area of the target tissue thus whereby tissues are more effectively transformed.

Additionally, there was a need for an improved whisker method that could be used with all of the target tissues that the regular method could be employed with such as type I, type II, type III callus or explants or scutella or zygotic embryos, protoplasts, hypcotyl or cotyledon derived callus, stomato cells, germline tissue, cell suspensions cultures and elite germplasm.

Although the whisker technology has undergone numerous technical achievements, including use of different types of target tissues like Type I and type two II callus or either elite or non-elite germplasm, forming commercially viable transgenic plants with the whisker method is still a laborious task. The method does not produce as many transformants per experiment as would be desirable when compared to using the gun technique. Whiskers low efficiency rate results in difficulties and added costs.

There remains a need for a modified method that will yield larger quantities of putative transformants than presently exists.

There also remains a need for an efficient whiskering method for transforming elite *Zea mays* germplasm.

There also remains a need for a more time efficient whisker method for transforming target tissue from wheat, barley, rye, soybeans, Brassica species, and grasses including perennial ryegrass, bentgrass and the like.

Additionally, there remains a need for a whisker method that may be employed to transform stomato cells or "guard cells" which are regenerable without the step of forming a protoplast.

BRIEF DESCRIPTION OF THE INVENTION

According to the present invention as herein disclosed, is an unexpected method for increasing the capacity of the whiskers system and a method for improving the number of transformants that result in transgenic plants. The present invention's improvement to this method is that the cocktail is shaken not stirred. In the previously known method the agitation step was a stirring, vortexing or mixing step. The present invention has unexpected realized that an agitation step of shaking in a robust fashion unexpectedly does not prove lethal to the cells. The resulting violent collisions between cells and the sharp silicon carbide "whiskers" result in the creation of small holes in the plant cell wall through which DNA enters the cell. Thereafter the method of the present invention parellels the known whisker method steps. Such steps being that those cells receiving and incorporating DNA are induced to grow and ultimately developed into fertile transgenic plants from which seed is harvested and new plants are bred and grown.

An object of the present invention is to provide an improved method to transform elite genotypes thus eliminating breeding steps associated with moving the gene into more desirable germplasm.

An object of the present invention is to provide an improved method for transformation of target cells, particularly plant cells.

One aspect of the present invention relates to a whisker method that permits large amounts of target tissue to be transformed more effectively resulting in a larger production of fertile, transgenic plants and the seeds and further progeny thereof containing DNA, originally introgressed by whiskers method into an ancestor plant wherein the DNA is heritable.

Another aspect of the invention is an improvement in the agitation of the whisker method that allows previously incompetent tissue (or tissue with very low transformant yield) to be more effectively transformed with whiskers.

An object of the present invention is to provide a method of whiskers transformation with an agitation means that more effectively accesses whiskers and DNA to most of the surface area of the target tissue.

Yet a further object of the present invention is to provide an improved whisker method that could be used on target tissue such as type I or type II or type III callus or explants or scutellar regions, stomato cells or cell suspensions cultures and elite germplasm.

The present invention also provides for an efficient whisker method for effectively transforming elite *Zea mays* germplasm.

Additionally a further aspect of the invention is providing whisker method for transforming target tissue from wheat, barley, rye, soybeans, Brassica species, and grasses including perennial ryegrass, bentgrass and the like.

Additionally, another objective of the present invention is providing a method of transforming stomato cells or "guard cells" which are regenerable without forming a protoplast.

Another object of the invention is use the results of the method to regenerate plants and seeds and the any progeny thereof and to breed, to select, to plant, to harvest or to produce harvestable products therefrom.

Another further object of the present invention is to provide a method of transforming with whiskers and DNA that is within a plasmid or is not within a plasmid.

Another further object of the present invention is to provide a method of transforming with whiskers and DNA that is a mix of DNA comprising at least two different cassettes (no plasmid is used referred herein also as linearized DNA) or within at least two different plasmids or a combination of cassettes and plasmids that are codelivered to the cells in the same whiskering method.

Yet a further object of the invention is to provide a method of transforming maize, wheat and sugarbeet stomatal cells callus without forming a protoplast prior to transformation.

One embodiment of the invention proves an improved method of introducing a nucleic acid into plant cells comprising providing a whisker cocktail comprising (i) at least one cell, (ii) a multiplicity of whiskers and (iii) at least one nucleic acid, and subjecting said whisker cocktail to a shaking motion of less than 2100 cycles per minute so as to create collisions between said whiskers and said plant cells whereby said nucleic acid is introduced into said plant cells.

This embodiment and each of the following embodiments can include the steps of regenerating at least one of said plant cells into a plant comprising said nucleic acid and/or using the seed or progeny which has an ancestor of the plant wherein said seed or progeny comprise through inheritance the nucleic acid directly or indirectly from the ancestor plant.

The embodiment can have cycles per minute which are less than 1000, the method preferably can have cycles per minute which are approximately 768.

One of the embodiments of the present invention is defining the vessel capacity that the present invention now allows to be employed. This embodiment provides a whisker mediated method for transforming a plant cell, said method comprising providing a whisker cocktail comprising: cells, a multiplicity of whiskers and DNA, contacting the cocktail in at least one vessel adapted to be shaken, wherein the vessel is capable of retaining at least 35 ml of said cells. This vessel is placed in means for shaking the cocktail; and, it is shaken with such shaking means wherein said DNA is capable of being inserted into at least one of said cells whereby forming a whisker mediated transformed plant cell.

Each of the embodiments of the present invention can be employed with all of the species and types of cells with which the original whiskering process could work. In many cases the present invention can be employed with even better clone production results. Thus each of the embodiments can be employed with monocots and dicots cells. And more specifically with cells from corn, wheat, rice, grasses including *Lolium perenne, Lolium multiflorum*, alfalfa, *Fes-* tuca arundinacea, Agrostis stolonifera, oryza sativa, tobacco, conifers, sunflower, brassica.

Additionally, the embodiments can employ different target tissue such as Type I callus, Type II callus, hypocotyl derived callus, cotyledon derived callus, stomato cells, meristem, scutella, callus derived from the scutellar region of the embryo, zygotic embryos, embroygenic callus, protoplasts, explants, germline tissue, suspension cell, type III callus.

One of the primary embodiment of the invention provides for the shaking movement. This embodiment provides a whisker mediated method for transforming a plant cell capable of being regenerated into a fertile plant, said method comprising providing a whisker cocktail comprising: cells, a multiplicity of whiskers and DNA; and shaking such cocktail in an nonrandom pathway in, at least two of the x axis, y and z axes wherein said DNA is capable of being inserted into at least one of said cells thus forming a whisker mediated transformed plant cell capable of being regenerated into a fertile plant.

Each of the various embodiments of the invention may include the step of regenerating at least one of said plant cells into a fertile plant. And optionally the step of harvesting seed from the fertile plant and using this seed in breeding or selection. More specifically the improved method includes the steps of planting the seed which form plants and selecting new seed from the plants and repeating the selection steps. Optionally these steps can be repeated. And this method as part of the ultimate goal of transformation includes the use of the seed or progeny which has an ancestor of the plant wherein said seed or progeny comprise through inheritance the nucleic acid directly or indirectly from the ancestor plant.

One embodiment of the invention is defined by its radius of movement. This embodiment provides a whisker mediated method for transforming a plant cell, said method comprising providing a whisker cocktail comprising (i) at least one cell, (ii) a multiplicity of whiskers and (iii) at least one nucleic acid, and haking such cocktail with means for shaking comprising an axis of rotation, wherein said shaking means extends such cocktail not less than 1.3 cm radially from said axis of rotation wherein said DNA is capable of being inserted into at least one of said cells thus forming a whisker mediated transformed plant cell.

The large volume permitted by the present improved whisker mediated method is shown in the embodiment where large volumes of plant cells are shaken in each respective whisker mediated shaking step, said method comprising providing a whisker cocktail comprising (i) not less than 48 ml of cells, (ii) a multiplicity of whiskers and (iii) at least one nucleic acid; and shaking such cocktail in a single whisker mediated transformation step wherein said DNA is capable of being inserted into said large volumes of plant cells thus forming whisker mediated transformed plant cells.

The embodiment of this invention can have cells (measured as packed seed volume (pcv) )in volumes of at least 70 ml and more preferably at least 105 ml. When the cocktail is placed into individual vessels the present invention includes at least a portion of said whisker cocktail being located in a vessel with not less than 3 ml of cells pcv.

In yet another embodiment of the invention there is provided an improved whisker mediated method for transforming a plant cell. In this improved method are the steps of contacting at least one cell with a multiplicity of whiskers and with DNA whereby forming a whisker cocktail; and shaking such cocktail in a nonrandom pathway in at least two of the x, y and z axes wherein said DNA is capable of being inserted into at least one of said cells thus forming a whisker mediated transformed plant cell.

In another one embodiment of the invention there is provided a whisker mediated method for transforming a plant cell: This method comprises the following steps: contacting at least one cell with a multiplicity of whiskers and with DNA whereby forming whisker cocktail; shaking such cocktail for at least 2 seconds wherein said DNA is capable of being inserted into at least one of said cells thus forming a whisker mediated transformed plant cell. Preferably the shaking is not longer then 59 seconds.

DETAILED DESCRIPTION OF THE INVENTION

Figure 1:
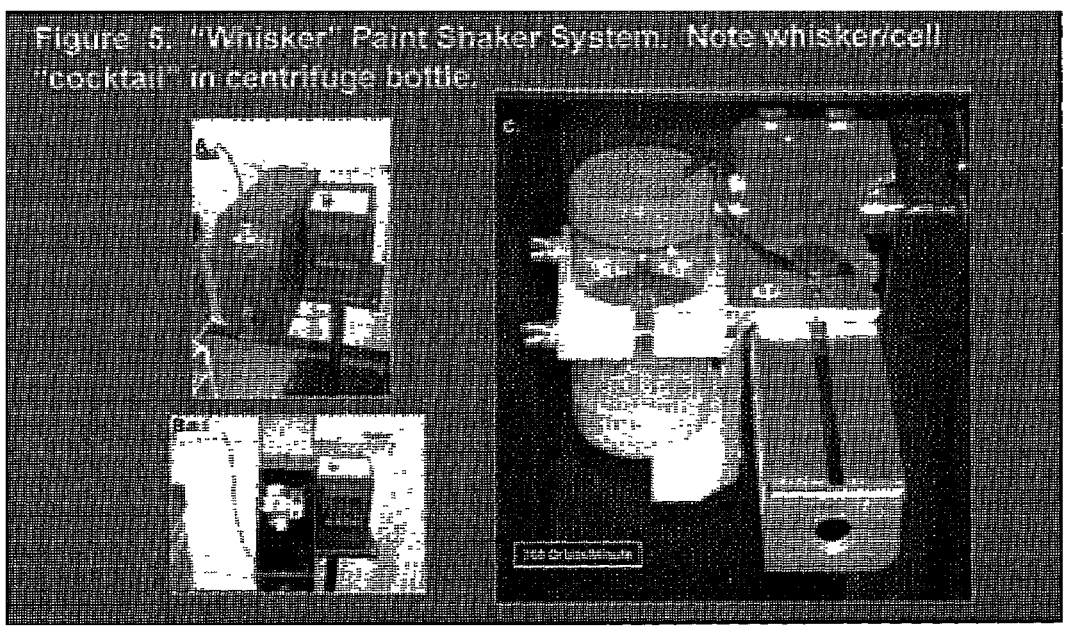
FIG. 1 is a picture of a modified red devil model 5400 paint shaker.

Whiskers refers to a genetic engineering technology for plant cells using small bits of silicon carbide or "whiskers". The technology is simple, providing a noncomplex DNA delivery method. The technology employs a small needle-like silicon carbide "whisker". Other material with the needle like shape could be employed. One type of Whiskers is available as Silar SC-9 from Advanced Composite Materials Corp. Greer S.C., USA. Whiskers are approximately 0.6 microns in diameter and 10-80 microns in length). Whiskers are used in a cell transformation method in the following manner. A cocktail is composed of DNA, cells and "whiskers" (other components can be added). The DNA can include for example genes, selectable marker gene, introns, promoters and the like in plasmids or without plasmids linearized. Cells for example can be embryogenic suspension tissue, callus of different types, or protoplasts.

In the standard whisker method taught in the earlier patents the cocktail is agitated by being stirred or vortexed to introduce DNA into the cells. The previous whisker method was not adapted for large quantities of plant target tissue.

In previous articles and patent literature concerning whisker mediated transformation the step of mixing the components of DNA and whiskers and cells was a standard step in the process. The mixing was done through stirring the components or vortexing the components. Both of these stirring actions tend to move the components in a vortex shaped pattern. This movement is usually forcing the components in a whirlpool action around the y axis. Stirring and vortexing substantially differ from the action of shaking the components.

It was discovered that use of a dental amalgam mixer moved the components principally within one axis in an osscillating movement. In this instance movement of the mixer was principally in the x axis with random movement into the Y or Z axes. This action is defined as a mixing action. This mixing action was a variation on the stirring and vortexing method of agitating the material. The mixing acted to create more collisions between the components whereby the DNA could be introduced into the plant cells. The present invention has further improved on the mixing action of the dental amalgam mixer.

The present invention is an improvement in the agitation step of the whisker mediated transformation method. The present invention moves the components principally within at least two axes of the X, Y or Z axes in a movement pattern that is not mixing or stirring or vortexing. This action is defined as a shaking action. Shaking motion of the present invention shall mean movement which is not solely stirring or vortexing but is a movement that agitates the components of the vessel into random, rapid collisions.

Shaking physical motion shall mean the motion that is substantially similar to the movement produced by a standard paint mixing machine such as the RED DEVIL® paint mixer apparatus model 5400. The present invention's shaking motion is in a nonrandom pathway in at least two of the x, y and z axes.

Furthermore, the present invention is operating this shaking action at less then 4200 cycles per minute which is the standard cycle per minute of the dental amalgam mixer. Additionally, the present device is working at less than 2100 cycles per minute which is the reduced number of cycles that a modification to the mixer has achieved. In fact, the shaking movement of the present invention operates very efficiently at less than 1000 cycles per minute. One of the embodiments of the present invention is adapted to run at approximately 768 cycles per minute(plus or minus 10) or lower as read by a is strobe tach.

It was highly surprising that although the present shaking step was operating at less the 1000 cycles per minute it still required substantially less agitation time to achieve the same or better clone production than did the dental amalgam mixer which ran at 2100 cycles per minute.

The agitation action of the present invention and the dental amalgam mixer further differs in that the present invention allows for substantially more radial movement from the axis of rotation. The present invention has more than a 1.3 cm radial movement off of the axis of rotation. The standard short arm extension used in the present invention allows more than a 4.3 cm radial movement off of the axis of rotation. The cocktail being moved approximatley 4 inches through the Y axis. As seen below in the technical data of the Mix o Mat is has a 2.5 cm Amplitude of oscillations appearing equivalent to approximately a 1.25 cm radial movement off of the axis of rotation.

In particular, the present invention is adapted to have varying adjustable positions which gives the invention differing lengths of radial movements from the axis of rotation.

This allows the components of the cocktail to fully collide with one another wherein the DNA can be inserted into the cells. It was highly surprising that with the greater range of movement around the axis of rotation that the present invention was not resulting in substantial amounts of lethal collisions within the cocktail.

The other discovery is that the same cellular material which worked with the standard whisker method can be employed in the improved method. But unexpectedly certain cells that were previously considered incompetent due to the low efficiency of stable clone recovery have using the present improvement sufficient stable clone recovery in shorter periods of time thus making these incompetent tissues competent. Examples include stomatal cells that are not protoplasts, germline material, scutellar regions and the like.

The resulting collisions between plant cells and "whiskers" are hypothesized to result in the creation of very small openings in the plant cell wall and membrane. As a consequence, the present improved shaking step provides for 1) DNA delivery into targeted plant cells, 2) chromosomal transgene integration, and ultimately, 3) transgenic clone/plant recovery.

In fundamental principle, this type of transformation utilizes a procedure which penetrates the cell wall in a non-lethal manner. The present invention delivers either single or multiple genes in this non-lethal manner. Southern analysis suggests that up to 47% of the transformation events may have single to low copy number insertions.

The method improvement of the present invention was reduced to practice with a modified "whisker"/cell collision system. More specifically, a commercial (Red Devil™) paint shaker was adapted and modified to create this collision system within very large batches of cocktail.

The modified step allows a single operator to process approximately 3 times the amount of tissue previously addressed, but still during a 2.5 hour period of time (equivalent to 255 bombardments when a biolistic gun system of transformation is used). 255 bombardments or the equivalent whiskered cells produced by the present invention under standard protocol for Whisker mediated transformation in 2.5 hours is defined as a commercially viable rate of clone production if more than 5% yield is reached (for particularly recalcitrant material 1% yield is acceptable). Thus, very large numbers of transgenic clones can be produced on a regular basis with the improvement of the present invention. The improvement of the present invention addresses a number of transformation concerns by 1) providing a robust approach that is adaptable to both low and high transformation efficiency cell lines, 2) reducing the cost of labor to produce transgenic clones, 3) maximizing transgenic clone output per unit of time, 4) addressing incompetent tissue inefficiency and 5) advancing breeding timelines through the coordinated development of large populations of unique T-0 transgenic plants that are very similar in maturity.

The original prior art whisker mediated processes relied on the use of a Vortex Genie™ or Dental Amalgam Mixer (Degusa Mix-O-Mat™) to perform a stirring or vortexing type of agitation with apparatus that limited the volume of material which could be transformed to relatively small volumes of "transformation cocktails". Previous cocktail volumes were less then 3 ml per vessel agitated. The prior art did not use in one shaking step a vessel that could hold more than 15 ml of material. Additionally, any one agitation step in the prior art would work with less then 50 ml total volume of cocktail. The prior art even at 4 times the standard of a 5% whiskers the weight used in the prior art of whiskers is 0.032 grams. In the prefered method of the present invention the use of 0.544 grams of whiskers is used.

In contrast, the improvement of the present invention provides in a single agitation step for the transformation processing of very large amounts of target tissue within larger amounts of cocktail, but with much shorter collision duration periods. The shaking step of the present invention requires minimized transformation inputs (time and labor) and maximizes clone production, particularly with recalcitrant cell lines.

The present invention like the method original is expected to produce stable transformed calli and/or plants in a variety of plants species such as *Zea mays* (4,5,8,9,10,13,16,17), *Lolium multiflorum, Lolium perenne, Festuca arundinacea, Agrostis stolonifera* (6), *Oryza sativa* (12), *Triticum aestivum* (2,14) and *Nicotiana tobacum* (10). See examples for Brassica and soybeans also.

The present invention like the method original is expected to produce stable transformed calli and/or plants from various cells for example Type I embryogenic maize callus, Type II embryogenic maize callus, type embryogenic maize III callus, hypocotyl derived callus, cotyledon derived callus, stomatal cells, meristem tissue, scutellar tissue, callus derived from the scutellar region of the zygotic embryo, zygotic embryos, embroygenic callus, germline tissue, suspension cell, Leaf Tissue, pollen, embyrogenic maize suspension tissue, regenerable suspension cells.

Whisker Transformation Protocol

The following is a general protocol for the "whisker" transformation processing of suspension or callus tissue with an embodiment of the device utilized in the method for the shaking step being a modified Red Devil™ paint shaker (FIG. 1). Another embodiment of the invention includes a method for shaking that is adapted for less than 2100 cycles per minute and standardly less then 1000 cycles per minute and most often at approximately 768 cycles per minute. Additonally the prefered embodiment is adjustable through 700 cycles per minute and more preferably less then 600 and even more preferably less than 500. The most prefered embodiment is variably adjustable to all cycles between 1000 and 350 cycles per minute.

The FIG. 1 paint shaker was modified to hold a 250 ml centrifuge bottle. This bottle, containing the "transformation cocktail" is extended not less than 1.3 cm radially from the axis of rotation and standardly is approximately 14 cm from the axis of rotation. The direction of rotation is an oval or FIG. 8 type orbit in at least two of the X, Y, and Z axes and usually in at all three of the X, Y, Z, axes. This shaking movement provides for more robust and more violent action than the prior art stirring or vortexing actions.

The following improved method according to the present invention describes the processing of at least 1 vessel of "whisker transformation cocktail". A single operator can process four vessels of target tissue with approximately 2.5 hours of effort.

EXAMPLE 1

Cell Line Development

Rapidly growing dispersed embryogenic suspension cell lines of A188/B73 were developed on N6-based medium (3) and maintained in liquid M.S. based medium (11) as described in Register et al. 1994. Friable elite callus cell lines are initiated and maintained on solid M.S. medium as reviewed in Bullock et al., 1998.

2. Cryo-preservation of Target Tissue

This step is optional and is not necessary nor critical to the invention. The cryo-process consists of mixing suspension or callus cells with a cryo-protectant consisting of 1 M Glycerol, 1 M DMSO, and 2 M Sucrose. This mixture is slowly cooled (0.5° C./minute) to −40° C. with a SY LAB Ice Cube 1600 Freezer™. Frozen tissue is then stored in liquid nitrogen at −196° C.

N6 Overnight Pre-treatment of Target Tissue

1 Combine 40 ml packed cell volume (P.C.V.) of target cells and conditioned M.S. liquid medium into one 1000 ml flask. Then re-aliquot 12 ml of P.C.V.+28 ml of conditioned M.S. liquid medium into each of 3 (500 ml) flasks that already contain 80 ml of fresh N6 liquid medium.

2. Culture the 3 flasks at 25° C. at 125 r.p.m. in the dark overnight.

3 B. Whisker Transformation

1. Draw off all N6 pre-treatment medium from the 3 overnight flasks. Add 72 ml N6 osmotic medium (containing 0.25 M mannitol and 0.25 M sorbitol) to each flask.

2. Osmotically pretreat for 45 minutes at 25° C. at 125 r.p.m.

3. Combine the contents (36 ml P.C.V.) from all 3 osmotic flasks into one 250 ml centrifuge bottle and allow the cells to settle well. Draw off 190 to 200 ml liquid and save for re-use.

4. Add 8.1 to 10.8 ml of a 5% whisker solution (5% w/v in liquid N6 Osmotic medium) and 170 ul of plasmid DNA to the centrifuge bottle+cells, and agitate on the paint shaker for the desired length of time (5-20 seconds).

5. Transfer all contents from the centrifuge bottle to the flask containing the N6 osmotic that was drawn off earlier.

6. Add 125-130 ml fresh N6 liquid (final total volume should be 375 ml) for a 2-hour post whiskering recovery period on a platform shaker (25° C., 125 r.p.m).

7. Isolate 15 ml of processed tissue suspension onto a filter paper (110 mm) using a poly Buchner funnel apparatus. Approximately 25 filters of tissue are derived from each bottle of whiskered tissue.

The filter was placed on an N6 solid medium plate with sterile forceps and the plates wrapped in 3M micropore tape. The platees were then incubated at 28° C. in the dark and examined for clones at 4,6,8 weeks after embedding.

Figure 2:
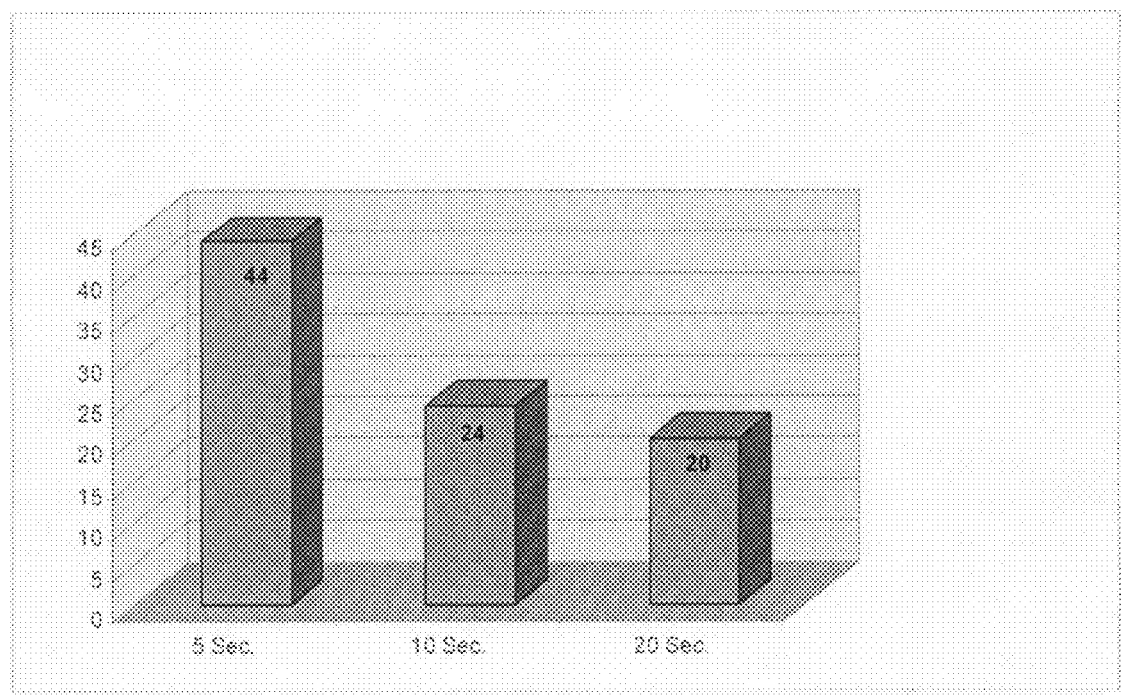
FIG. 2 is a graph showing transgenic clone recovery as a function of shaking duration with the paint shaker system. Axis x of the graph represents Shaking Duration and axis Y represents PCR+ Clone Recovery. The material shaken was 36 ml P.C.V. of cells, 85 mg of DNA, 5.4 ml of a 5% whisker solution, 14 ml of liquid N6 medium.

Commercially competent cell lines must be able to produce adequate numbers of regenerable transgenic clones that ultimately result in the production of fertile transgenic plants. For example when 35 ml of PVC cells are employed an adequate numbers of clones for one whisker mediated transformation with the shaking movement of the present invention is 10 PCR positive clones, and more preferably 20 and yet more preferably 24 and yet more preferable 40 and above (see FIG. 2).

The above Table employed 36 ml PCV (packed cell volume), 85 ug of DNA and 5.4 ml of 5% whisker solution and 14 ml of liquid medium. The duration of the whiskering process impacts transgenic clone production. Optimum periods of time for experiments one and two on corn lines are 1 minute for the dental amalgam mixer and 5-20 seconds for the present invention when the shaking motion is provided with the paint shaker system (FIG. 1).

EXAMPLE 2

Prior Art Agitation Method using a Dental Amalgam Mixer System

The "whisker" transformation protocol given in example 1 was employed with the modification being that a prior art method of agitation such as that type of agitation provided by the Dental Amalgam "Mix-O-Mat™" was used. The amalgamator shaft moves back and forth in an X axis and somewhat randomly in the Y and Z axes at about 2100 orbits per minute. Due to the difference in the agitation method used by the prior art the agitation step although having more cycles per minute the device in experiment one required an agitation time period of 1 minute. In this example the limitation of the agitation step required that all the quantities of all components were reduced accordingly to match the final volume of 2 ml P.C.V of target tissue, 160 ul to 640 ul of a 5% solution of whiskers in N6 medium, and 1 ml of liquid N6 osmotic medium per 15 ml centrifuge tube. The result was a single operator processed about ⅓ the amount of target tissue with this system during a similar 2.5 hour period of transformation effort.

EXAMPLE 3

Whisker Transformation Parameters for the Shaker Improvement

Using the standard protocol given in experiment one it has been discovered that further improvements to the present invention can be 1) target tissue pre-treatment, 2) varying the ratio of the "transformation cocktail" components (cells, DNA, whiskers), and 3) whisker/cell collision duration appear to directly impact transgenic clone production.

Experimentation indicated that transferring suspension target tissue from M.S.-based suspension medium to liquid N6-based medium overnight results in a significant enhancement in clone production. Experimentation indicated that reduced DNA quantities (5-10 micro-grams/2 ml P.C.V of target tissue) enhanced transgenic clone recovery.

Evaluation of whisker concentration suggested increasing the total amount of silicon carbide whiskers is beneficial to transgenic clone production. Optimum amounts of whiskers varies with method and cell line, but 320 ul and 8.1 ml of a 5% whisker solution produce large numbers of transgenic clones in our maize suspension cell lines. No DNA delivery has been observed without inclusion of whiskers in the "transformation cocktail".

EXAMPLE 3

Elite Maize Embryogenic Suspension and Zygotic Embryo Scutellar Cells

Cell Line Transformation Competence and Time Line

Cell lines such as elite corn lines vary in 1) transformation competence, 2) regeneration capacity, and 3) fertility in regenerant plants compared to AXB cell. As a consequence, 2-3 cryo-derived cell lines from known "good" cryo-sources were used as controls during each round of transformation using the shaking motion of the present invention according to the protocol given above.

Both suspension (A188×B73) and callus (Stiff Stalk Inbred) being from zygotic embryo scutellar cells were transformed using the present improvement to the "whiskers" methodology. Transgenic clone production with Stiff-Stalk inbred callus cell lines is substantially lower, but the use of the paint shaker approach provides a means to compensate for the lower inherent transformation capacity of this type of target tissue.

Transgenic callus clones were isolated approximately 1.5 to 3 months' post DNA delivery. An additional 1.5 to 3 months were required for plant regeneration. Therefore, these suspension and callus lines required, on average, about 10 months to progress from DNA delivery to seed harvest.

EXAMPLE 4

Transgene Insertion Analysis

Southern Analysis

Copy number estimation was done in two different ways. In the first method, transgenic maize genomic DNA (12 ug per lane) was digested with a restriction enzyme that cuts only once in the plasmid used in transformation. The number of bands generated is a clue to the number of copies and insertion pattern in this method.

In the second method, plant DNA was digested with a restriction enzyme that cuts out the gene of interest (2.1 kb). Copy number can be estimated by the intensity of the bands compared to lanes containing non-transgenic DNA spiked with plasmid DNA in the equivalent of 1, 5, and 10 copies of the gene of interest (+1, +5, +10). Negative control DNA (N) is non-transformed maize DNA. The Southerns were done according to the protocols given Maniatis et al.(1981).

Southern analysis of over 100 transformation events produced in experiments 1 and 3 indicated that the improvement to whisker transformation system produced reasonable frequency of low copy transformation events. Approximately 47% of 100 Southern analyzed transformation events have 1-3 copies of the selectable marker gene.

Lower copy number is an added benefit as the possibilities of gene silencing are reduced as are the difficulties associated with regulatory approval and breeding and introgression of the DNA into new lines through inheritance and breeding.

Additionally, the previous method for whisker-mediated transformation needed an improved way to transformation incompetent plant target tissue.

The present invention which is in one embodiment formed as a scale-up modified paint shaker machine provides for the whisker transformation (U.S. Pat. No. 5,302, 526 and U.S. Pat. No. 5,464, 765) of large amounts of plant cell target tissue. Since the system capacity has been greatly increased, improved efficiencies of transgenic callus clone and plant production are the result. Since large amounts of tissue can be processed, very large numbers of transgenic calli and plants can be produced in a very short period of time.

As noted above, target tissues low in transformation competence can be used for plant transformation more effectively. That is, whisker processing of large amounts of target tissue will result in the re-definition of competence in that lines previously believed to be incompetent for whiskers transformation may now be utilised and considered a competent. Very large amount of minimally competent tissue can now be processed and this results in reasonable transgenic callus clone and plant production. This new shaking approach provides significant benefits in terms of advancing transformation program timelines. For example, instead of requiring a substantial period of time to produce a large number of transformation events, this approach now provides for the production of large numbers of transgenic callus clones all a one time. This results in more co-ordinated seed production (with respect to a multiplicity of events) and better fits the demands of filed plantings where only a certain window of time is available for plating. More transformation events can be planted and evaluated at the same time in the field.

When using the standard Whiskers protocol, it is very time-consuming to prepare and work with up to 24 small (15 ml) tubes for each experiment. Use of one or two large vessels for the agitation segment of the Whiskering process is more feasible. The shaker most often employed is the commercial paint shaker (Red Devil) which has been modified such that an arm, connection to the shaker rotating axis, has attached to it an adjustable clamping system. Containers of various sizes and containing the whisker transformation cocktail can be secured on the arm via the container—clamping device see FIG. 1. Further, the position of the claming device is variable with respect to its position on the arm. Thus, the severity of the shaking and plant cell/whisker collisions can be varied by moving the position of the clamping device closer to or further away from the end of the arm. The longest setting is 10.5 inches from the axis of rotation. One of the short setting is 6.5 inches from the axis of rotation. In addition, the speed of the paint shaker and the duration of the whisker collision process are modified to affect plant cell/whisker collisions.

The invention will now be described, by way of illustration, in the following:

Experiment 1: Increased Volume of Cells to be Transformed

Purpose. To evaluate bulking up the volume of cells per unit of whisker mediated transformation.

Protocol

| | |
|---|---|
| Cell line | A5D1-C149 |
| Plasmid | pGAR5 |
| Plasmid concentration | 8 µl equivalent |
| Whiskers concentration | 2x equivalent |
| Container | 250 ml polycarbonate centrifuge bottle |
| Shaking apparatus | Red Devil paint mixer with adaptation |

The decision was made to change only the size of the vessel used to agitate the cells, with all other steps in the process remaining the same. That way we could evaluate the vessel and shaking movement of the machine alone, without involving any other variables.

Preparation of Cells

Cells were put into N6 liquid medium the day before the Whisker process was to be used, per standard protocol. It was estimated to require 12 flasks at 3 ml PCV, for each 250 ml container, so we prepared 24 flasks of cells for the two bottles. On the morning of the experiment, all cells and N6 media were combined in a 1000 ml flask, mixed well, and re-aliquoted into N6 osmotic liquid, 2 ml PCV of cells per 125 ml osmotic flask (also standard protocol). Two sets of osmotic flasks were done, 20-25 minutes apart. These were put on the platform shaker for the standard 45-minute osmotic treatment.

Combining the Components and Agitation

Approximately 10-13 minutes before the end of the osmotic treatment, all cells and media from one set of 18 osmotic flasks were transferred to the centrifuge bottle. The cells were allowed to settle and the liquid was drawn off down to the 50 ml mark. This gave us approximately the same ratio of cells and liquid: total volume as the 15 ml tubes (1:5). Whiskers were added at the rate of 5360 µl per bottle. Eighty-five microliters of plasmid was added, the bottle was capped and sealed with Parafilm, and shaken on the Red Devil paint shaker for 60 seconds.

Description of the Paint Shaker Adaptations:

An extension for the shaker arm was fabricated so that the centrifuge bottle could be clamped at a number of distances from the axis of rotation. The shaker arm, as originally designed, moved in a narrow figure-eight pattern, which was not altered in any way by the changes to the arm. We chose to test two positions on the arm: one at either extreme of the adjustment slot. Total distance from the axis for setting A (the shorter setting) was 6.5 inches; distance for setting B (the longer setting) was 10.5 inches.

Post-agitation Treatment:

Cells and medium from the shaken bottle were placed in a 500 ml flask, along with all the osmotic liquid that had been removed before agitation. Regular N6 liquid medium was added at the rate or 153 ml par flask (approximately 375 ml total volume) for a 2-hour recovery. This differs slightly in proportion of cells: liquid from the standard Mixomat, because we weren't able to fit the proper amount of liquid in the flask. Once the two hours was about up, the cells were plated in 4.5 ml aliquots using the standard #4 Whatman fitter papers with the cell collector filtration apparatus. The filter papers were placed on 60×20 mm plates of N6 solid medium for recovery. Only a total of 12 plates were prepared from each bottle, with 4 for transient assay and 8 for regrowth evaluation and stable clone recovery.

Two tubes of cells were given standard whiskers treatment, to be used as standards, against which to gauge efficiency of the experimental protocol.

GUS Histochemical Transient Expression Assay:

The assay was done 72 hours post-DNA delivery, frozen for approximately 60 minutes, incubated overnight at 37 degrees C., and counted the next day.

Stable Clone Recovery:

The remaining 18 plates of cells were treated exactly according to standard post-transformation whiskers protocol, from the 3-week recovery and selection period, to embedding, to three picking dates 4, 6 and 8 weeks post-embedding.

Results:

Treatment A=average Color forming unit (CFU) 3412-short arm position

Treatment B=average Color forming unit (CFU) 3180-long arm position

Treatment C=average Color forming unit (CFU) 1670-Standard Mix o mat*

* DEGUSSA MIXOMAT Technical Data

| | |
|---|---|
| Power consumption | 220 VA (50 Hz) |
| 140 VA (60 Hz) | |
| Dimensions (H*/W/D) | 220/210/210 mm |
| Mixing frequency | 4200 min −1 +/− 120 min −1 |
| Amplitude of oscillations | 25 mm |
| Mode of operation | STO 20% WT |
| CT 8 min | |
| Adjustable mixing time range | 1 . . . 99 sec |

Discussion:

It appears that there is little or no difference in transient expression between the two settings on the arm of the paint shaker. There is only a 7.3% increase in cfu's when the bottle is moved to the shorter setting, a negligible increase when compared with total cfu's. There is, however, a great difference in transient expression between the paint shaker and the standard Mixomat. Cfu counts for both settings on the paint shaker are double the average for two tubes whiskered via standard protocol.

The cell aggregates on the paint shaker plates seemed to be smaller in size than those on the control plates, an indication that the different (and possibly more violent) motion of the paint shaker causes aggregates to break up, giving more overall surface area for the whiskers to collide with.

Conclusions:

The modified Red Devil paint shaker with large volumes of cells and whiskers is a suitable alternative to the Mixomat.

Experiment 1a

GUS ASSAY RESULTS

| Tube/Bottle | CFU | Average for Unit | Average for Treatment | Treatment description |
|---|---|---|---|---|
| A2 | 3047 | 3412 | 3412 | short-arm position on paint shaker |
| A9* | 4262 | | | |
| A12* | 3520 | | | |
| A3* | 2818 | | | |
| B6* | 3580 | 3180 | 3180 | long-arm position on paint shaker |
| B8* | 3226 | | | |
| B | 2550 | | | |
| B | 3362 | | | |
| C13 | 1409 | 1575 | 1670 | standard mixomat A |
| C1 | 1740 | | | |
| C22 | 1756 | 1765 | | |
| C2 | 1774 | | | |

Paint Shaker Experiment 2

Time Comparison

Purpose

The experiment was to determine the optimum duration for shaking on the paint shaker at one position on the shaking arm.

Protocol

Cell Line: A5D1-C149
Plasmid: pGAR5
Plasmid concentration: 8 ul equivalent
Whiskers concentration: 2× equivalent
Container: 250 ml polycarbonate centrifuge bottle
Shaking apparatus: paint shaker (per Experiment 1a)
Bracket position of paintshaker: B (longest setting)

Treatments:

| | |
|---|---|
| A | 15 seconds |
| B | 30 seconds |
| C | 45 seconds |
| D | 60 seconds |

All steps were identical to those in Experiment 1a, except: 1) forty-eight N6 flasks were prepared the day before; 2) the volume of cells and liquid was too great for one 1000 ml flask, so half of the cells were combined in each of two 500 flasks and 3) there were four sets of osmotic flasks, each at least 30 minutes apart to allow for proper manipulation of the cells. Twenty plates were prepared from each of the four treatments. Five plates went to GUS histochemical assay. GUS assay was done 48 hours post-transformation.

Results and Discussion

Transient Expression Results

Experiment 2

GUS Assay Results

| Treatment | Plate Name | CFU's | Average CFU Count for Treatment |
|---|---|---|---|
| 15 seconds | A21 | 2566 | 2478 |
| | A22 | 770 | |
| | A23 | 3026 | |
| | A25 | 3548 | |
| 30 seconds | B7 | 2480 | 3142 |
| | B8 | 3100 | |
| | B9 | 3824 | |
| | B10 | 3162 | |
| 45 seconds | C3 | 2708 | 2543 |
| | C6 | 1898 | |
| | C13 | 2766 | |
| | C20 | 2800 | |
| 60 seconds | D2 | 3546 | 2323 |
| | D5 | 1776 | |
| | D7 | 2370 | |
| | D18 | 1600 | |

While there was a wide range of transient expression within all the treatments, it seems that 30 seconds gave the best average cfu (color forming units) count. The numbers for this treatment were also the most consistent of all the treatments. The reason this treatment gave the best results could be that at 15 seconds, there was not enough time for as many collisions to occur and at the longer times there was more cell damage.

Experiment 3

Time Comparison II

Purpose:

To 1) further optimize the duration of shaking with the Red Devil modified paint shaken and 2) evaluate a scale—up of the plating process.

Background:

In Experiment 2, we concluded that time points above 30 seconds resulted in lower transient expression levels as well as a somewhat slower rate of regrowth. The arm length was shortened. There was better regrowth from cells shaken at the shorter distance from the axis (setting A).

Protocol:
Cell Line: A5D1-C149
Plasmid: pGAR5 (pCATII+pUNI-GUS)
Plasmid concentration: 5 μl equivalent
Whiskers concentration: 2× equivalent
Container: 250 ml polycarbonate centrifuge bottle
Shaking apparatus: paint shaker (as per Experiment 1)
Bracket position of paintshaker: A(Ishortest arm length setting)

Treatments

| | |
|---|---|
| A | 5 seconds |
| B | 10 seconds |
| C | 20 seconds |

All steps in the process through the recovery were according to shaker-mediated transformation protocol as previously described. The plating went as follows:
1. Four plated per bottle were plated onto the standard whisker-size plates (60×20 mm) at 4.5 ml per plate. These went to GUS array for transient expression.
2. The remainder or the cells were plated on filter papers cut to approximately fit the 100×15 plates normally used for embedding. Aliquots of 12.5 ml whiskered cells and medium per plate were used. This gave 28 plates per bottle, for a total or 84 plates for the whole experiment. GUS assay was done 72 hours post-transformation on all small plates. All larger plates went to stable clone recovery.

Results and Discussion

Transient Result
GUS Assay Results

| GUS Assay Results | | |
|---|---|---|
| Treatment | Plate Name | CFU Count* |
| 5 seconds | A1 | 1988 |
| | A2 | 1912 |
| | A3 | 2050 |
| | A4 | 1768 |
| | Average for treatment | 1925 |
| 10 seconds | B1 | 2290 |
| | B2 | |
| | B3 | 2470 |
| | B4 | 2148 |
| | Average for treatment | 2303 |
| 20 seconds | C1 | 2734 |
| | C2 | 2604 |
| | C3 | 3606 |
| | C4 | 2808 |
| | Average for treatment | 2888 |

There was a direct relationship between shaking duration and level of transient expression. While the increases are not great, there was a definite increase in average cfu counts with increased shaking time.

For treatment A using a different cell line C149 with short arm length for:

| Treatment | Plate | Clones | Positive GUS |
|---|---|---|---|
| 5 seconds | 28 medium plates | 46 | 6 |
| 10 seconds | 28 medium plates | 25 | 5 |
| 20 seconds | 28 medium plates | 17 | 5 |

Experiment 4

Volume of Whiskers

Purpose:
To assemble all components as they will be used for future production whiskering, and to compare the "standard" paint shaker 1× volume to a doubled, or 2× volume.

Protocol

Cell Line: A5D1-C152
Plasmid: pGAR5
Plasmid concentration: 5 ul equivalent
Whiskers concentration: 2× equivalent
Container: 250 ml polycarbonate centrifuge bottle
Apparatus: Red Devil modified paint shaker
Bracket position: A (shortest arm lenght)
Filter apparatus: polypropylene Buchner funnel assembly
Filter paper size: 110 mm (Whatman #4 papers)
N6 overnight/N6 osmotic flask size: 500 ml
Recovery plate size: 150×15 mm Treatments:

A "standard" total volume: 5400 ul whiskers, 84 ul plasmid B 100 ml total volume (same cell: total ration as standard); 1080 u whiskers, 168 ul plasmid.

The volumes for the N6 treatment were changed from the standard, but the cell: total Ratio was equivalent. Fifteen ml of cells plus 35 ml conditioned H9CP+ were places in 100 ml N6 in a 500 ml flask, for a total of 150 ml. The N6 treatment was 48 hours long for this experiment. On experiment day, all cells and liquid were combined in one 1000 ml flask, and aliquoted from there into osmotic medium. Osmotic treatment was altered in manner similar to the N6 overnight treatment. Twelve ml of cells was added to 72 ml of N6 gusmotic liquid in the 500 ml flasks, giving the same ratio as the standard, Mixomat version.

Since there was now more liquid in treatment B (480 ml total) than the centrifuge bottle could hold, a portion of the N6 was drawn off periodically during the combining phase. Care was taken to keep track of how much was added in and drawn off so the final volume was correct.

Transient assay was done on both treatments. Eight small plates (60×20 mm) were prepared from each bottle or GUS assay, done 48 hours post-whiskering. Ten large (150×15 mm) plates were prepared from each bottle for stable clone recovery.

Plating volume for stable clone plates was 15 ml per filter paper.

| Experiment | Treatment | # of Plates Available | # of Clones Picked |
|---|---|---|---|
| #4 (2/23/2000) | a) C152, PGAR5/5 ul short arm, 20 sec, 1X total volume | 10 large | 12 |
| | b) 2X total volume | 10 large | 7 | small: 80 mm
Medium: 90 mm
Large: 110 mm

The results of a similar type of experiment where the standard of measure was a herbicide resistance gene and not a color forming gene.

| Treatment All according to the shaking step of the present invention | # of Plates Available | Conversion to Mixomat Plate Equivalents | # of Clones Sampled for PCR | # Clones PCR + PAT |
|---|---|---|---|---|
| A) C149, pGAR5/5 ul, short arm, 60 sec. | 8 small | 8 | 0 | 0 |
| B) C149, pGAR5/5 ul, long arm, 60 sec. | 8 small | 8 | 1 | 1 |
| A) C149, pGAR5/5 ul, short arm, 15 sec. | 15 small | 15 | 2 | 2 |
| B) 30 sec. | 15 small | 15 | 2 | 2 |
| C) 45 sec. | 15 small | 15 | 4 | 3 |
| D) 60 sec. | 15 small | 15 | 1 | 1 |
| A) C152, pGAR5/5 ul, short arm, 5 seconds | 28 medium | 63 | 47 | 44 |
| B) 10 seconds | 28 medium | 63 | 25 | 24 |
| C) 20 seconds | 28 medium | 63 | 22 | 21 |
| A) C152, short arm, 20 sec., pCATII/ 10 ul | 28 medium | 63 | 89 | 87 |
| B) 20 ul | 28 medium | 63 | 61 | 61 |
| A) C152, pGAR5/5 ul, short arm, 20 sec., 1X total volume | 10 large | 33.6 | 21 | 18 |
| B) 2X total volume | 10 large | 33.6 | 12 | 10 |
| Totals | | 458.2 | 287 | 274 |

Clearly the results show that PCR positive transformants are developed by the present invention. Additionally, these are regenerated into fertile transgenic plants and seed is harvested therefrom.

Experiment 5

Whisker Transformation Competency of Elite Cell Cultures

A. Thawing

Embryos were not available for culture immediately, so elite maize cultures of BE81 and BE70 that had been cryopreserved several years ago were thawed. A total of 11 BE81 lines and 12 BE70 lines were thawed onto N6 solid media.

B. Regrowth 6 lines from each genotype grew back fairly well on the filter paper so were transferred directly to N8 media to attempt to bulk them. Half of the callus was transferred to media containing AgNO3 (61-1) BE81-65 (81-1/TIII), BE81-88 (N6 TII version and TIII version) and BE70-27 (N6/TIII). All three grew extremely well.

C. Transformation

Treatments:

Standard (N6 liquid overnight, 45 minute osmotic pretreatment, 320 ul whiskers, 20 ul DNA mixed 60 seconds. The same experiment as experiment one (except for the callus) is employed. The experiment using the paint shaker will recover clones.

Plasmid: pCATII

Protocol:

Callus was mixed into 100 ml N6 liquid media (14 plates of callus) After the cells were broken up by pipetting, 2 ml pc was places into a flask with ml N6 for overnight. Before experimentation, the N6 was drawn off and 12 ml of N6 osmoticum was added to each flask for pretreatment. A standard suspension experiment with standard whisker protocol.

Results:
80715S: no clones per 60 plates
80826S: Treatment A-3 clones per 35 plates (8.6%)

Experiment 6

Whiskering Different Types of Callus (TII/TIII) for Transformation.
Cell Line:
Maize elite BE81-68 (#2)
BE81-65 (#4 and #7)
Plasmid: pCATII
Protocol:
The protocol was the same as above using TII, TII (8 plates of callus for each)

Results:
80812S: Treatment A-5 clones per 50 plates (10%)
Treatment C-1 clones per 30 plates (3,3%)
PCR results of experiments 5 and 6 and another experiment on elite resulted with 33 of these clones. The results for the pat gene show all 33 of the 33 to be PCR positive.

Regeneration:
As the clones are bulked up they are put into regeneration. 17 clones have begun regeneration. We have obtained 4 plantlets. In general the BE81 clones appear to a bit more regenerable than the BE70.

Experiment 7

1. Suspensions
Elite suspension could be transformed. A suspension of BE81-68 TII tissue was developed in H9CP+media. Three whisker experiments have been completed. All were standard whisker experiments as used for A×B suspensions. 13 putative clones have been picked.

Experiment 8

Transforming Wheat with Standard Whiskers.
Cell Line: callus of wheat var. "Bobwhite" (obtained from T. Weeks in Nebraska)
Plasmid: pUB-GUS
Method Treatment:
Callus cultures were maintained on a 2-week transfer schedule. Cultures were maintained in 16 h light. The maintenance media was MS with 2% sucrose, 1.5 mg/L 2,4-D, and 0.2% gelrite.
Two treatments were used for this experiment:
1. Cells put into N6 liquid overnight: Cells were bulked up by pipetting. 2 ml pcv was aliquotted into each of two 125 ml Erlenmeyer.
2. Cells left on solid maintainance media.
Four plates of callus was used for each treatment.

Day 1 (Experiment Day):
After pretreatment, the cells were treated according to standard.
2 ml cells/1 ml liquid in a 15 ml centrifuge tube
20 ul plasmid DNA
320 ul whiskers (5% w/v with N6 osmotic media)
60 second mix on mix-o-mat A 2 h recovery with 18 ml N6 (non-osmotic)
Plated at 6 ml/plate onto N6 solid Results
GUS assay performed at 48 h post-whiskering.
Treatment 1: Rep 1-57, 57, 58 cfu's
  Rep 2-50, 32, 34 cfu's
Treatment 2: Rep 1-0, 0, 2 cfu's
  Rep 2-0, 1, 0 cfu's While the cfu's are very low, we can get DNA into wheat callus with the whiskers technology. The improvement of the present invention is believed to be capable of substantially increasing the efficiency of whiskering wheat callus.

Experiment 9

Soybeans and Stomato Cells of Sugarbeet with Prior Art Whiskering Technique.

Soybean cultures and stomato cells of sugar beet could also be so transferred with our whiskers technology. Again transformation was determined by histochemical gus assay.

A. Experiment Soybean:
Cell Line: c90 soybean suspensionis (was obtained from J. Finer at Ohio State University)
Also A cell line of a sugarbeet stomato cell callus is generated according to description by Robert Hall (no protoplast were formed)
Plasmid: pAID-Aubq-Gus (pGAR3)
Method/Treatment:
Cells were maintained on a 1-week transfer schedule. 1 ml pcv of cells was transferred to 33 ml of fresh FN media in 125 ml Erlenmeyer flask.

For whiskering, approximately 25 ml of cells were combined and 2 ml pcv aliquots were placed into 25 ml Erlenmeyer flasks with 12 ml FN osmotic media (FN with 0.25M sorbitol/0.25M mannitol) for 45 minutes. After pretreatment the cells were whiskered according to a modified maize suspension whisker protocol:
  2 ml cells/1 ml liquid in a 15 ml centrifuge tube
  20 ul DNA
  1 minute mixing
  2 h recovery with non-osmotic media
The following treatments were utilized:
Tubes E-H: 320 ul whiskers
Tubes U-Z: 640 ul whiskers The cells were plated on Whatman #4 filters onto FN solid media at 6 ml/plate. Two plates were plated per tube. Gus assay done at 48 hr post-whiskering.

Few spots were visible, but the results show DNA in soybean cells using Whiskers technology. The structure of the soyean callus is hard and large. This is perfect for the improved shaking method. Better results are anticipated with the paint shaker.

Gus Assay Results From Whiskering of Soybean Cultures

| Gus assay results from whiskering of soybean cultures | |
| --- | --- |
| Tube ID | Total Cfu's/trt |
| A (320, L2) | 5 |
| E (320, M2) | 11 |
| I (320, H2) | 19 |

| Gus assay results from whiskering of soybean cultures | |
| --- | --- |
| Tube ID | Total Cfu's/trt |
| M (640, L2) | 7 |
| Q (640, M2) | 22 |
| U (640, H2) | 16 |

Whisker transformation can occur in soybean cells. It is believed that sugar beet stomato callus will likewise give positive results.

Experiment 10

Canola by Original Whiskering Method
Experimental design
Plasmid PAC402 2×DNA, Ix=20 ul
MM time+1 min.
Whiskers 2×, 1×=160 ul
48 hr. Gus Assay

| Tube | tissue vol. | B5 Osm. Vol. | PCV + med | B5 recovery vol. | Total | plates |
| --- | --- | --- | --- | --- | --- | --- |
| A | 0.75 ml | 9.0 ml | 3.0 ml | 13.5 ml | 22.5 ml | 4 |
| B | 2.0 ml | 12.0 ml | 3.0 ml | 18.0 ml | 30.0 ml | 5 |

| Gus Assay results | | | |
| --- | --- | --- | --- |
| Tube | ID | Plate | Canola #CFU's |
| A | 2-1-1 | 1 | 3 |
|   |   | 2 | 15 |
|   |   | 3 | 0 |
|   |   | 4 | 12 |
|   |   | 5 | ? |
| B | 2-2-1 | 1 | 26 |
|   |   | 2 | 10 |
|   |   | 3 | 33 |
|   |   | 4 | 13 |
|   |   | 5 | 30 |

It is evident that canola is also transformable with whiskers. It has been our experience that each cell type that has been transformed with the standard protocol is as transformable and most often more transformable with the present improvement to the whisker method.

Experiment 11

Transgenic Seed and Progeny Production Using Present Invention

Stable transformation of embryogenic suspension tissue was conducted by colliding embryogenic suspension cells of maize (A188/B73) with Silicon Carbide Whiskers (Advanced Composite Materials Corporation, Greer, S.C., SC-9 type, 0.5 micron average diameter and 10-80 microns in length) in the presence of selectable marker gene (DNA). This mixture of transformation competent maize cells, whiskers and DNA is referred to as a "transformation cocktail"

A Red Devil™ paint shaker was modified to hold a 250 ml centrifuge bottle. The bottle, containing the "transformation cocktail" is extended approximately 14 cm from the axis of rotation on the paint shaker. The direction of rotation is an oval orbit in X, Y, and Z axes and this shaking system reaches a speed of approximately 768 cycles per minute.

This below described transformation methodology was replicated 3 times to process 3 bottles of "transformation cocktail" during a single experiment.

A. N6 Overnight Pre-treatment of Target Tissue
1. Combine 40 ml packed cell volume (P.C.V.) of target cells and conditioned M.S. liquid medium into one 1000 ml flask. Then re-aliquot 12 ml of P.C.V.+28 ml of conditioned M.S. liquid medium into each of 3 (500 ml) flasks that already contain 80 ml of fresh N6 liquid medium.
2. Culture the 3 flasks at 25° C. at 125 r.p.m. in the dark overnight.

B. Whisker Transformation
1. Draw off all N6 pre-treatment medium from the 3 overnight flasks. Add 72 ml N6 osmotic medium (containing 0.25 M mannitol and 0.25 M sorbitol) to each flask.
2. Osmotically pretreat for 45 minutes at 25° C. at 125 r.p.m.
3. Combine the contents (36 ml P.C.V.) from all 3 osmotic flasks into one 250 ml centrifuge bottle and allow the cells to settle well. Draw off 190 to 200 ml liquid and save for re-use.
4. Add 8.1 to 10.8 ml of a 5% whisker solution and 170 ul of plasmid DNA to the centrifuge bottle+cells, and agitate on the paint shaker for the desired length of time (5-20 seconds).
5. Transfer all contents from the centrifuge bottle to the flask containing the N6 osmotic that was drawn off earlier.
6. Add 125-130 ml fresh N6 liquid (final total volume should be 375 ml) for a 2-hour post whiskering recovery period on a platform shaker (25° C., 125 r.p.m).
7. Isolate 15 ml of processed tissue suspension onto a filter paper (110 mm) using a poly Buchner funnel apparatus. Twenty-five filters of tissue were derived from each bottle of whiskered tissue.

In Vitro Selection.

Transgenic callus clone selection methodology was similar to that described in Register et al. (1994) and Frame et al. (1994). Whisker transformation efficiency with respect to stable PCR-positive (selectable marker gene) callus clone are illustrated in Table 1.

TABLE 1

| Bottle | No. of Plates in Selection | No. of PCR Positive Callus Clones | Efficiency |
|---|---|---|---|
| 1 | 25 | 5 | 20% |
| 2 | 25 | 4 | 16% |
| 3 | 25 | 10 | 40% |
| Total/Average | 75 | 19 | 25% |

Plant Regeneration.

Plant regeneration was conducted in a similar fashion to that described in Register et al. (1994) and Frame et al. (1994). Young plants were transferred to the greenhouse and pollinated. T-O seed were produced from regenerant plants representing 8 of the 19 callus clones.

EXAMPLE 12

Inbred Corn Line

An embryogenic suspension of an inbred corn line was subjected to the whiskering transformation process as described above. In this case, experiments were conducted repeatedly over several weeks. PCR positive clones (selectable marker gene) transgenic callus clones were produced as illustrated in Table 2.

| No. of Plates in Selection | No. of PCR Positive Callus Clones | Efficiency |
|---|---|---|
| 708 | 73 | 10.3% |

Several of these transgenic callus clones were regenerated

REFERENCES

1. Bullock, W. P., D. Foster, T. Friend, A. Greenland, D. Dias, and V. Kaster. Transgene silencing in maize: phenotypic segregation analysis. 1998. Illinois Plant Breeder School Proceedings: 157-190.
2. Brisibe, E. A., A. Gajdosava, A. Olesen, and S. B. Andersen. 2000. Cytodifferentiation and transformation of embryogenic callus lines derived from anther culture of wheat. Journal of Experimental Botany 51: 187-196.
3. Chu, C. C., C. C. Wang, C. S. Sun, C. Hsu, K. C. Yin, C. Y. Chu, F. Y. Bi. 1975. Establishment of an efficient medium for anther culture of rice through comparative experiments on nitrogen sources. Sci. Sinica. 18:659-668.
4. Coffee, R., and J. M. Dunwell. 1994. Transformation of plant cells. U.S. Pat. No. 5,302,523.
5. Coffee, R., and J. M. Dunwell. 1995. Transformation of plant cells. U.S. Pat. No. 5,464,765.
6. Dalton, S. J., A. J. E. Bettany, E. Timms, and P. Morris. 1997. Transgenic plants of Lolium multiflorum, Lolium perenne, Festuca arundinacea, and Agrostis stolonifera by silicon carbide fibre-mediated transformation of cell suspensions. Plant Science 132: 31-43.
7. Dunahay, T. G., 1993. Transformation of Chlamydomonas reinhardtii with silicon carbide whiskers. Biotechniques 15: 452-460.
8. Frame, B., P. Drayton, S. Bagnall, C. Lewnau, P. Bullock, M. Wilson, J. Dunwell, J. Thompson, and K. Wang. 1994. Production of fertile transgenic maize plants by silicon carbide whisker mediated transformation. The Plant Journal 6: 941-948.
9. Kaeppler, H. F., W. Gu, D. A. Somer, H. W. Rines, and A. Cockburn. 1990. Silicon carbide fiber-mediated DNA delivery into plant cells. Plant Cell Reports 9:415-418.
10. Kaeppler, H. F., D. A. Somers, H. W. Rines, and A. Cockburn. 1992. Silicon carbide fiber-mediated stable transformation of plant cells. Theoretical and Applied Genetics. 84: 560-566.
11. Murashige, T. and F. Skoog, 1962. A revised medium for rapid growth and bioassays with tobacco tissue cultures. Physiol. Plant. 15: 473-497.
12. Nagatani, N., H. Honda, T. Shimada, and T. Kobayashi. 1997. DNA delivery into rice cells and transformation using silicon carbide whiskers. Biotechnology Techniques. 11: 471-473.
13. Petolino, J. F., Hopkins, N. L., Kosegi, B. D., Skokut, M., 2000. Whisker mediated transformation of embryogenic callus of maize. Plant Cell Reports 19 (8): 781-786.
14. Serik, O., I. Ainur., K. Murat, M. Tetsuo, and I. Masaki. 1996. Silicon carbide fiber-mediated DNA delivery into cells of wheat (Triticum aestivum L.) mature embryos. Plant Cell Reports 16: 133-136.

15. Register, J. C., D. J. Petterson, P. J. Bell, W. P. Bullock, I. J. Evans, B. Frame, A. J. Greenland, N. S. Higgs, I. Jepson, S. Jiao, C. J. Lewnau, J. M. Sillick, and H. M. Wilson. 1994. Structure and function of selectable and non-selectable transgenes in maize after introduction by particle bombardment. Plant Molecular Biology 23: 951-961.
16. Thompson, J. A., P. R. Drayton, B. R. Frame, K. Wang, and J. M. Dunwell. 1995. Maize transformation utilizing silicon carbide whiskers: a review.
17. Wang, K., P. Drayton, B. Frame, J. Dunwell, and J. A. Thompson. 1995. Whisker-mediated plant transformation: An alternative technology. In Vitro Cellular and Developmental Biology 31: 101-104.

We claim:

1. A method of introducing at least one nucleic acid into at least one plant cell comprising the steps of: providing a whisker cocktail comprising (i) at least one cell, (ii) a multiplicity of whiskers and (iii) at least one nucleic acid, and the improvement comprising employing a device with a shaking action said whisker cocktail with a shaking motion of less than 1000 cycles per minute and more than 350 cycles per minute, for 5-20 seconds, so as to create collisions between said whiskers and said plant cells whereby at least one of said nucleic acid is introduced into at least one of said plant cells.

2. The method according to claim 1 including a step of regenerating at least one of said plant cells into a plant comprising said nucleic acid.

3. The method according to claim 2 including a step of using the regenerated plant to produce seed.

4. The method according to claim 1 wherein said cycles per minute are approximately 768.

5. A whisker mediated method for transforming a plant cell, said method comprising:
   (a) providing a whisker cocktail comprising: cells, a multiplicity of whiskers and DNA,
   (b) contacting said cocktail in at least one vessel adapted to be shaken;
   (c) placing at least one of such vessels holding the cocktail in a paint mixer machine adapted for shaking the cocktail; and,
   (d) shaking with such paint mixer at least one of such vessels for 5-20 seconds with a shaking motion of less than 1000 cycles per minute. wherein said DNA is inserted into at least one of said cells whereby forming a whisker mediated transformed plant cell.

* * * * *